United States Patent
Ozaki et al.

(10) Patent No.: US 10,005,701 B2
(45) Date of Patent: Jun. 26, 2018

(54) SUPPORT FOR SUPPORTING METALS, METAL-SUPPORTED CATALYST, METHANATION REACTION APPARATUS, AND METHOD RELATING TO THESE

(71) Applicants: NATIONAL UNIVERSITY CORPORATION GUNMA UNIVERSITY, Maebashi, Gunma (JP); NISSHINBO HOLDINGS INC., Tokyo (JP)

(72) Inventors: Jun-ichi Ozaki, Kiryu (JP); Hiroki Takahashi, Yoshioka-machi (JP); Takuya Takahashi, Aichi (JP); Naokatsu Kannari, Kiryu (JP); Rieko Kobayashi, Sano (JP); Naoto Saito, Tokyo (JP)

(73) Assignees: NATIONAL UNIVERSITY CORPORATION GUNMA UNIVERSITY, Gunma (JP); NISSHINBO HOLDINGS INC., Tokyo (JP)

( * ) Notice: Subject to any disclaimer, the term of this patent is extended or adjusted under 35 U.S.C. 154(b) by 235 days.

(21) Appl. No.: 14/359,815

(22) PCT Filed: Nov. 1, 2012

(86) PCT No.: PCT/JP2012/078385
§ 371 (c)(1),
(2) Date: May 21, 2014

(87) PCT Pub. No.: WO2013/077165
PCT Pub. Date: May 30, 2013

(65) Prior Publication Data
US 2014/0296357 A1   Oct. 2, 2014

(30) Foreign Application Priority Data
Nov. 25, 2011 (JP) .................. 2011-257842

(51) Int. Cl.
*C07C 1/04* (2006.01)
*B01J 23/755* (2006.01)
(Continued)

(52) U.S. Cl.
CPC ............. *C07C 1/0435* (2013.01); *B01J 23/75* (2013.01); *B01J 23/755* (2013.01); *B01J 35/002* (2013.01); *B01J 35/006* (2013.01); *C01B 3/586* (2013.01)

(58) Field of Classification Search
None
See application file for complete search history.

(56) References Cited

U.S. PATENT DOCUMENTS

| 5,488,023 A | 1/1996 | Gadkaree et al. |
| 7,560,496 B2 * | 7/2009 | Kuhrs ............... B01J 21/18 518/714 |

(Continued)

FOREIGN PATENT DOCUMENTS

| JP | A-03-093602 | 4/1991 |
| JP | A-11-086892 | 3/1999 |

(Continued)

OTHER PUBLICATIONS

McIntyre et al.; New Interpretations of XPS Spectra of Nickel Metal Oxides; Surface Science; 600, 1771-1779; 2006.*
(Continued)

*Primary Examiner* — Guinever S Gregorio
(74) *Attorney, Agent, or Firm* — Oliff PLC

(57) ABSTRACT

Provided are a support for supporting a metal, a metal-supported catalyst, a methanation reaction apparatus, and a method relating thereto that realize effective methanation of carbon monoxide. The support for supporting a metal includes a carbonized material obtained by carbonizing raw materials containing an organic substance and a metal, in (Continued)

which the support is used for supporting a metal that exhibits a catalytic activity for a methanation reaction of carbon monoxide. The metal-supported catalyst includes: a support formed of a carbonized material obtained by carbonizing raw materials containing an organic substance and a metal; and a metal that exhibits a catalytic activity for a methanation reaction of carbon monoxide, the metal being supported on the support.

14 Claims, 7 Drawing Sheets

(51) Int. Cl.
  *C01B 3/58* (2006.01)
  *B01J 35/00* (2006.01)
  *B01J 23/75* (2006.01)

(56) References Cited

U.S. PATENT DOCUMENTS

| | | |
|---|---|---|
| 2008/0139676 A1 | 6/2008 | Kuhrs et al. |
| 2008/0292530 A1 | 11/2008 | Keller et al. |
| 2011/0229766 A1 | 9/2011 | Ozaki et al. |

FOREIGN PATENT DOCUMENTS

| | | |
|---|---|---|
| JP | A-2002-068707 | 3/2002 |
| JP | A-2008-056539 | 3/2008 |
| JP | A-2008-528250 | 7/2008 |

OTHER PUBLICATIONS

Translation of Jun et al.; Thermal Decomposition of AP Catalyzed by Carbon-Coated Iron, Cobalt and Nickel Nano-Composite Materials; Oct. 13, 2006.*

Feb. 12, 2013 International Search Report issued in International Patent Application No. PCT/JP2012/078385.

May 27, 2014 English-language International Preliminary Report on Patentability issued in International Patent Application No. PCT/JP2012/078385.

Synthesis, Properties and Applications of Carbon Encapsulated Metal Nanoparticles, Master Degree Thesis of Wuhan Institute of Technology, section 1.2.2, p. 5, published on May 1, 2009.

Influence of ferrocene addition on the morphology and structure of carbon from petroleum residue, carbon, vol. 41, pp. 3037-3046, published on Dec. 31, 2003.

Oct. 19, 2016 Office Action issued in Chinese Patent Application No. 201280057832.6.

Zhao, Jun et al. "Thermal Decomposition of AP Catalyzed by Carbon-Coated Iron, Cobalt and Nickel Nano-Composite Materials." Chinese Journal of Explosives & Propellants, vol. 29, No. 5, pp. 35-38, 2006.

* cited by examiner

|  | Ni PARTICLE SIZE (nm) | Ni CRYSTALLITE SIZE (nm) |
|---|---|---|
| Ni/NSC | 5.5 | 5.0 |
| Ni/XC | 5.5 | 3.6 |
| Ni/LY | 5.0 | 3.9 |

FIG.8A
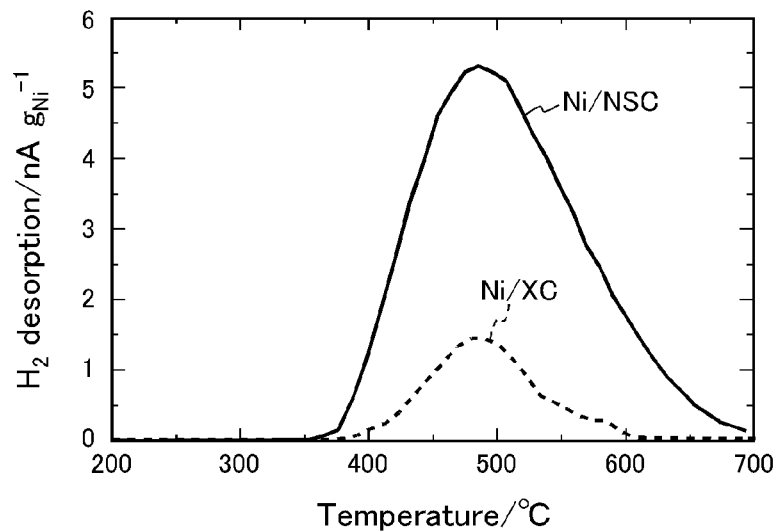
FIG.8B
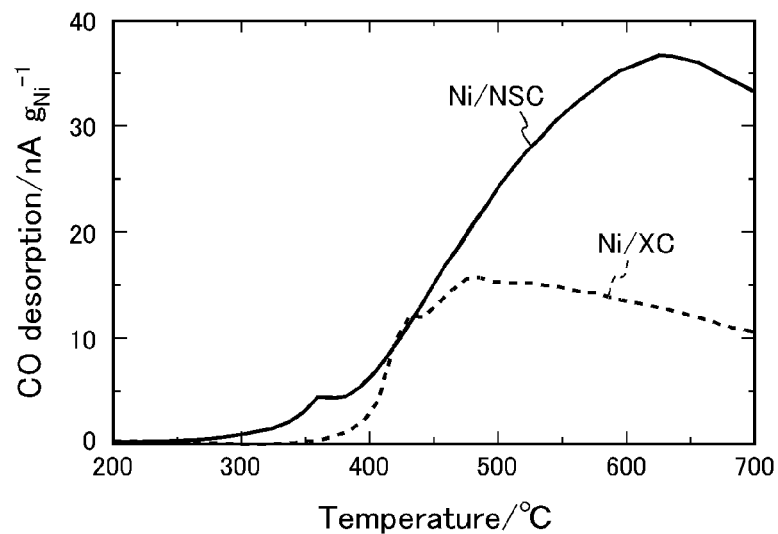
FIG.9
|  | CO DESORPTION AMOUNT (mmol/g-Ni) | H$_2$ DESORPTION AMOUNT (mmol/g-Ni) | H$_2$/CO RATIO (-) |
|---|---|---|---|
| Ni/NSC | 6.3 | 4.3 | 0.68 |
| Ni/XC | 3.9 | 0.8 | 0.21 |

SUPPORT FOR SUPPORTING METALS, METAL-SUPPORTED CATALYST, METHANATION REACTION APPARATUS, AND METHOD RELATING TO THESE

TECHNICAL FIELD

The present invention relates to a support for supporting a metal, a metal-supported catalyst, a methanation reaction apparatus, and a method relating thereto, and more particularly, to methanation of carbon monoxide.

BACKGROUND ART

Hydrogen ($H_2$) to be used as a fuel in an anode of a fuel cell is obtained through steam reforming from a hydrocarbon-based fuel such as liquefied natural gas (LNG), liquefied petroleum gas (LPG), naphtha, gasoline, kerosene, or light diesel oil, an alcohol-based fuel such as methanol, or city gas.

A reformed gas obtained through the steam reforming contains, in addition to hydrogen, carbon monoxide (CO) at a significant concentration. The CO contained in the reformed gas causes various problems in the fuel cell. Accordingly, it is necessary to decrease the carbon monoxide concentration in the reformed gas as much as possible before the reformed gas is supplied to the fuel cell.

To that end, hitherto, as one of the methods of decreasing the CO concentration, there has been proposed a method involving converting carbon monoxide into methane (methanation of carbon monoxide) (for example, Patent Literatures 1 to 4).

CITATION LIST

Patent Literature

[PTL 1] JPH 03-093602 A
[PTL 2] JPH 11-086892 A
[PTL 3] JP 2002-068707 A
[PTL 4] JP 2008-056539 A

SUMMARY OF INVENTION

Technical Problem

However, the activity of the related-art catalyst for methanation is not necessarily sufficient.

The present invention has been made in view of the problem, and one of the objects of the present invention is to provide a support for supporting a metal, a metal-supported catalyst, a methanation reaction apparatus, and a method relating thereto that achieve effective methanation of carbon monoxide.

Solution to Problem

A support for supporting a metal according to one embodiment of the present invention for achieving the above-mentioned object includes a carbonized material obtained by carbonizing raw materials containing an organic substance and a metal, in which the support is used for supporting a metal that exhibits a catalytic activity for a methanation reaction of carbon monoxide. According to the one embodiment of the present invention, a support for supporting a metal that achieves effective methanation of carbon monoxide is provided.

In addition, in the support for supporting a metal, the metal that exhibits a catalytic activity for a methanation reaction of carbon monoxide may include one or more kinds selected from the group consisting of Ni, Ru, Rh, Pd, Pt, Ir, Cu, W, Cs, K, Na, Co, Fe, Ca, Mg, Ba, Sr, and Li. In this case, the metal that exhibits a catalytic activity for a methanation reaction of carbon monoxide may include Ni.

In addition, the support for supporting a metal, when supporting Ni, may have: a ratio of a peak area in a range of from more than 853.5 eV to 860 eV or less to a peak area in a range of from 850 eV or more to 860 eV or less of 0.5 or more, the peak areas being obtained by XPS measurement of an electron state of 2p orbitals of the Ni; and a molar ratio of an $H_2$ desorption amount in a range of from 40° C. to 800° C., which is obtained by an $H_2$ temperature-programmed desorption method, to a CO desorption amount in a range of from 40° C. to 800° C., which is obtained by a CO temperature-programmed desorption method, of 0.3 or more.

A metal-supported catalyst according to one embodiment of the present invention for achieving the above-mentioned object includes: a support formed of a carbonized material obtained by carbonizing raw materials containing an organic substance and a metal; and a metal that exhibits a catalytic activity for a methanation reaction of carbon monoxide, the metal being supported on the support. According to the one embodiment of the present invention, a metal-supported catalyst that achieves effective methanation of carbon monoxide is provided.

In addition, in the metal-supported catalyst, the metal that exhibits a catalytic activity for a methanation reaction of carbon monoxide may include one or more kinds selected from the group consisting of Ni, Ru, Rh, Pd, Pt, Ir, Cu, W, Cs, K, Na, Co, Fe, Ca, Mg, Ba, Sr, and Li. In this case, the metal that exhibits a catalytic activity for a methanation reaction of carbon monoxide may include Ni.

In addition, the metal-supported catalyst may have: a ratio of a peak area in a range of from more than 853.5 eV to 860 eV or less to a peak area in a range of from 850 eV or more to 860 eV or less of 0.5 or more, the peak areas being obtained by XPS measurement of an electron state of 2p orbitals of the Ni; and a molar ratio of an $H_2$ desorption amount in a range of from 40° C. to 800° C., which is obtained by an $H_2$ temperature-programmed desorption method, to a CO desorption amount in a range of from 40° C. to 800° C., which is obtained by a CO temperature-programmed desorption method, of 0.3 or more.

A methanation reaction apparatus according to one embodiment of the present invention for achieving the above-mentioned object includes any one of the metal-supported catalysts, in which the methanation reaction apparatus is used for a methanation reaction of carbon monoxide. According to the one embodiment of the present invention, a methanation reaction apparatus that achieves effective methanation of carbon monoxide is provided.

A method according to one embodiment of the present invention for achieving the above-mentioned object includes using, as a support for supporting a metal that exhibits a catalytic activity for a methanation reaction of carbon monoxide, a carbonized material obtained by carbonizing raw materials containing an organic substance and a metal. According to the one embodiment of the present invention, a method that achieves effective methanation of carbon monoxide is provided.

In addition, in the method, the metal that exhibits a catalytic activity for a methanation reaction of carbon monoxide may include one or more kinds selected from the group consisting of Ni, Ru, Rh, Pd, Pt, Ir, Cu, W, Cs, K, Na, Co, Fe, Ca, Mg, Ba, Sr, and Li. In this case, the metal that exhibits a catalytic activity for a methanation reaction of carbon monoxide may include Ni.

A method according to one embodiment of the present invention for achieving the above-mentioned object includes performing a methanation reaction of carbon monoxide using any one of the metal-supported catalysts. According to the one embodiment of the present invention, a method that achieves effective methanation of carbon monoxide is provided.

In addition, the method may include treating a first gas containing carbon monoxide to produce a second gas whose concentration of carbon monoxide is decreased compared to that of the first gas. In this case, the first gas and the second gas may each further contain hydrogen. In addition, the method may use a methanation reaction apparatus including the metal-supported catalyst.

A method according to one embodiment of the present invention for achieving the above-mentioned object is a method of selecting, from a plurality of candidate supports, a support for supporting a metal that exhibits a catalytic activity for a methanation reaction of carbon monoxide, the method including: determining, for each of the plurality of candidate supports in a state of supporting Ni, whether or not a ratio of a peak area in a range of from more than 853.5 eV to 860 eV or less to a peak area in a range of from 850 eV or more to 860 eV or less, the peak areas being obtained by XPS measurement of an electron state of 2p orbitals of the Ni, is equal to or higher than a threshold set in advance of 0.5 or more; determining, for each of the plurality of candidate supports in a state of supporting Ni, whether or not a molar ratio of an $H_2$ desorption amount in a range of from 40° C. to 800° C., which is obtained by an $H_2$ temperature-programmed desorption method, to a CO desorption amount in a range of from 40° C. to 800° C., which is obtained by a CO temperature-programmed desorption method, is equal to or higher than a threshold set in advance of 0.3 or more; and selecting, from the plurality of candidate supports, a support for which it is determined that the ratio of the peak areas is equal to or higher than the threshold, and the molar ratio is equal to or higher than the threshold. According to the one embodiment of the present invention, a method that achieves effective methanation of carbon monoxide is provided.

Advantageous Effects of Invention

According to embodiments of the present invention, a support for supporting a metal, a metal-supported catalyst, a methanation reaction apparatus, and a method relating thereto that achieve effective methanation of carbon monoxide are provided.

BRIEF DESCRIPTION OF DRAWINGS

FIG. 8A is an explanatory diagram showing examples of the results of evaluation of metal-supported catalysts by an $H_2$ temperature-programmed desorption method in an Example according to one embodiment of the present invention.

FIG. 8B is an explanatory diagram showing examples of the results of evaluation of the metal-supported catalysts by a CO temperature-programmed desorption method in an Example according to the one embodiment of the present invention.

FIG. 9 is an explanatory diagram showing examples of the results of evaluation of the $H_2$ desorption amounts and CO desorption amounts of the metal-supported catalysts in an Example according to the one embodiment of the present invention.

DESCRIPTION OF EMBODIMENTS

Figure 1A:
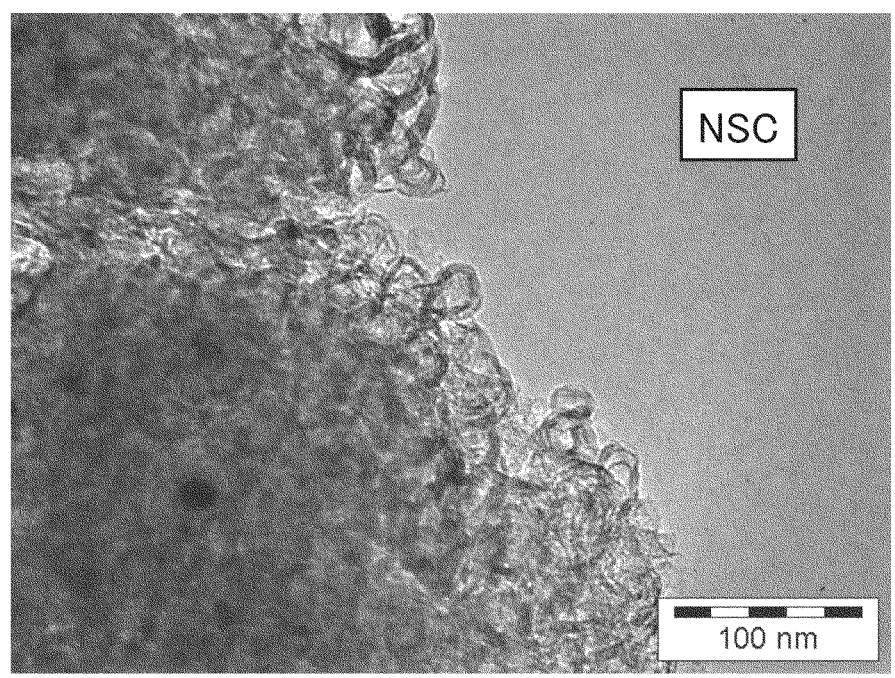
FIG. 1A is an explanatory diagram showing an example of the result of observation of a support for supporting a metal according to one embodiment of the present invention with a transmission electron microscope.

Hereinafter, embodiments of the present invention are described. It should be noted that the present invention is not limited to examples shown in these embodiments.

A support for supporting a metal according to one embodiment of the present invention (hereinafter referred to as "support of the present invention") is a support formed of a carbonized material obtained by carbonizing raw materials containing an organic substance and a metal, the support being used for supporting a metal that exhibits a catalytic activity for a methanation reaction of carbon monoxide. That is, the carbonized material constituting the support of the present invention is obtained by carbonizing the raw materials containing the organic substance and the metal.

The organic substance contained in the raw materials is not particularly limited as long as the organic substance can be carbonized. That is, as the organic substance, for example, there may be used a high-molecular-weight organic compound (for example, a resin such as a thermosetting resin and/or a thermoplastic resin) and/or a low-molecular-weight organic compound. In addition, biomass may also be used as the organic substance.

The organic substance may be a nitrogen-containing organic substance. The nitrogen-containing organic substance is not particularly limited as long as it is an organic substance containing an organic compound containing in its molecule a nitrogen atom, and any one or more kinds of nitrogen-containing organic substances may be used.

The organic substance may contain a ligand capable of coordinating with a metal. The ligand is, for example, a compound containing in its molecule one or more ligand atoms. Examples of the ligand atom may include one or more kinds selected from a group consisting of a nitrogen atom, a phosphorous atom, an oxygen atom, and a sulfur atom. In addition, an example of the ligand is a compound having one or a plurality of ligand groups in its molecule. Examples of the ligand group may include one or more kinds selected from a group consisting of an amino group, a phosphino group, a carboxyl group, and a thiol group.

As the organic substance, there may be used, for example, one or more kinds selected from a group consisting of a phenol resin, polyfurfuryl alcohol, furan, a furan resin, a phenol formamide resin, melamine, a melamine resin, an epoxy resin, a chelate resin, a polyamide imide resin, pyrrole, polypyrrole, polyvinyl pyrrole, 3-methyl polypyrrole, acrylonitrile, polyacrylonitrile, a polyacrylonitrile-polymethacrylic acid copolymer, polyvinylidene chloride, thiophene, oxazole, thiazole, pyrazole, vinylpyridine, polyvinylpyridine, pyridazine, pyrimidine, piperazine, pyran, morpholine, imidazole, 1-methylimidazole, 2-methylimidazole, quinoxaline, aniline, polyaniline, succinic acid dihydrazide, adipic acid dihydrazide, polysulfone, polyaminobismaleimide, polyimide, polyvinyl alcohol, polyvinyl butyral, benzimidazole, polybenzimidazole, polyamide, polyester, polylactate, polyether, polyether ether ketone, cellulose, carboxymethylcellulose, lignin, chitin, chitosan, pitch, lignite, silk, wool, polyamino acid, a nucleic acid, DNA, RNA, hydrazine, a hydrazide, urea, salen, polycarbazole, polybismaleimide, triazine, polyacrylic acid, polyacrylate, polymethacrylate, polymethacrylic acid, polyurethane, polyamide amine, and polycarbodiimide.

The metal contained in the raw materials is not particularly limited as long as the metal does not inhibit the activity of a metal-supported catalyst obtained by supporting a metal that exhibits a catalytic activity for a methanation reaction of carbon monoxide on the support of the present invention. That is, for example, there may be used one or more kinds of metals selected from a group consisting of metals belonging to Group 3 to Group 16 of the periodic table.

In this case, one or more kinds selected from a group consisting of Group 3A (Group 3) elements, Group 4A (Group 4) elements, Group 5A (Group 5) elements, Group 6A (Group 6) elements, Group 7A (Group 7) elements, Group 8 (Group 8, Group 9, and Group 10) elements, Group 1B (Group 11) elements, Group 2B (Group 12) elements, Group 3B (Group 13) elements, Group 4B (Group 14) elements, Group 5B (Group 15) elements, and Group 6B (Group 16) elements of the periodic table may be used, transition metals (Group 3 to Group 12 of the periodic table) may be preferably used, and transition metals belonging to the fourth period of Group 3 to Group 12 of the periodic table may be more preferably used.

Specifically, there may be preferably used, for example, one or more kinds of metals selected from a group consisting of scandium (Sc), titanium (Ti), vanadium (V), chromium (Cr), manganese (Mn), iron (Fe), cobalt (Co), nickel (Ni), copper (Cu), zinc (Zn), yttrium (Y), zirconium (Zr), niobium (Nb), molybdenum (Mo), ruthenium (Ru), rhodium (Rh), palladium (Pd), lanthanides (such as cerium (Ce)), and actinides.

As the metal, there may be used an elementary substance of the metal or a compound of the metal. As the metal compound, for example, one or more kinds selected from a group consisting of a metal salt, a metal oxide, a metal hydroxide, a metal nitride, a metal sulfide, a metal carbide, and a metal complex may be used, and one or more kinds selected from the group consisting of a metal salt, a metal oxide, a metal sulfide, and a metal complex may be preferably used. It should be noted that when the organic substance described above contains a ligand, a metal complex is formed in the raw materials.

In addition, the metal contained in the raw materials may be a metal of a different kind from that of a metal that exhibits a catalytic activity for a methanation reaction of carbon monoxide to be supported on the support of the present invention. That is, the metal contained in the raw materials may be, for example, a transition metal of a different kind from that of the metal that exhibits a catalytic activity for a methanation reaction of carbon monoxide to be supported on the support of the present invention. The amount of the metal contained in the raw materials is not particularly limited, and for example, the weight ratio of the metal to the organic substance contained in the raw materials may be 1 to 15 wt %.

The raw materials are prepared by mixing the organic substance and the metal. A method of mixing the raw materials is not particularly limited, and for example, a mortar or a stirring apparatus may be used. In addition, there may be used one or more kinds of mixing methods such as: powder mixing involving mixing the organic substance and metal in powder forms; and solvent mixing involving mixing the organic substance and the metal with a solvent added thereto.

The carbonization of the raw materials is performed by heating the raw materials and keeping the raw materials at a predetermined temperature at which the raw materials are carbonized (carbonization temperature). The carbonization temperature is not particularly limited as long as the raw materials are carbonized at the temperature, and for example, the carbonization temperature may be 300° C. or more. More specifically, the carbonization temperature may be, for example, 300° C. or more and 1,500° C. or less.

A rate of temperature increase in the heating of the raw materials to the carbonization temperature is not particularly limited, and for example, may be 0.5° C./min or more and 300° C./min or less. A period of time for which the raw materials are kept at the carbonization temperature is not particularly limited as long as the raw materials are carbonized in the period of time, and for example, the period of time may be 5 minutes or more, or may be 5 minutes or more and 240 minutes or less. In addition, the carbonization is preferably performed under an inert gas such as nitrogen (for example, under a stream of the inert gas).

The carbonized material formed by the carbonization of the raw materials as described above may be directly used as the support of the present invention. In addition, the support of the present invention may be formed of a pulverized carbonized material. A method of pulverizing the carbonized material is not particularly limited, and for example, there may be preferably used a pulverizing apparatus such as a ball mill or a bead mill. The average particle size of the carbonized material after the pulverization may be, for example, 150 µm or less.

The support of the present invention may be formed of a carbonized material subjected to metal-removing treatment. The metal-removing treatment is treatment for removing a metal contained in the carbonized material and derived from the raw materials. The metal-removing treatment is not particularly limited as long as the treatment removes the metal contained in the carbonized material or decreases the amount of the metal, and for example, washing treatment with an acid or electrolytic treatment may be performed.

The acid to be used for the washing treatment with an acid is not particularly limited as long as an effect of the metal-removing treatment is obtained, and any one or more kinds of acids may be used. That is, for example, there may be used one or more kinds selected from a group consisting of hydrochloric acid (for example, dilute hydrochloric acid and concentrated hydrochloric acid), nitric acid (for example, dilute nitric acid and concentrated nitric acid), and sulfuric acid (for example, dilute sulfuric acid and concentrated sulfuric acid). A method for the washing treatment with an acid is not particularly limited, and for example, there may be preferably used a method involving immersing and keeping the carbonized material in a solution containing the acid.

The metal to be supported on the support of the present invention is not particularly limited as long as the metal catalyzes a methanation reaction of carbon monoxide. Examples thereof may include one or more kinds selected from a group consisting of Ni, Ru, Rh, Pd, Pt, Ir, Cu, W, Cs, K, Na, Co, Fe, Ca, Mg, Ba, Sr, and Li.

In addition, for example, when supporting Ni as a metal that exhibits a catalytic activity for a methanation reaction of carbon monoxide, the support of the present invention may have: a ratio of a peak area in the range of from more than 853.5 eV to 860 eV or less to a peak area in the range of from 850 eV or more to 860 eV or less, the peak areas being obtained by XPS measurement of the electron state of the 2p orbitals of the Ni, (hereinafter referred to as "XPS peak area ratio") of 0.5 or more; and a molar ratio of an $H_2$ desorption amount in the range of from 40° C. to 800° C., which is obtained by an $H_2$ temperature-programmed desorption method, to a CO desorption amount in the range of from 40° C. to 800° C., which is obtained by a CO temperature-programmed desorption method, (hereinafter referred to as "$H_2$/CO ratio") of 0.3 or more.

In this case, for example, the XPS peak area ratio may be 0.6 or more, or may be 0.7 or more. The upper limit value of the XPS peak area ratio is not particularly limited, and for example, the XPS peak area ratio may be 1.0 or less, or may be less than 1.0.

In addition, for example, the $H_2$/CO ratio may be 0.4 or more, may be 0.5 or more, or may be 0.6 or more. The upper limit value of the $H_2$/CO ratio is not particularly limited, and for example, the $H_2$/CO ratio may be 5 or less.

Efficient methanation of carbon monoxide is achieved by using, as the support for supporting a metal that exhibits a catalytic activity for a methanation reaction of carbon monoxide as described above, the carbonized material obtained by carbonizing the raw materials containing the organic substance and the metal described above.

That is, in general, when a methanation reaction of carbon monoxide is performed using a metal-supported catalyst obtained by supporting a metal on a support, methane formed is decomposed over the reaction time, resulting in the deposition of carbon on the surface of the metal. Consequently, the catalytic activity of the metal is decreased or lost in some cases. In this regard, the use of the carbonized material as the support for the metal effectively suppresses the deposition of carbon on the surface of the metal due to the decomposition of methane.

Further, the inventors of the present invention have made extensive studies on the improvement of the activity of a catalyst for methanation. As a result, the inventors themselves have found that the carbonized material constituting the support of the present invention effectively improves the methanation catalytic activity of a metal supported on the carbonized material.

That is, for example, when the support of the present invention exhibits the XPS peak area ratio and $H_2$/CO ratio described above, the methanation catalytic activity of the metal supported on the support of the present invention is particularly effectively enhanced.

A metal-supported catalyst according to one embodiment of the present invention (hereinafter referred to as "catalyst of the present invention") is a catalyst including: a support formed of a carbonized material obtained by carbonizing raw materials containing an organic substance and a metal (that is, the support of the present invention described above); and a metal that exhibits a catalytic activity for a methanation reaction of carbon monoxide, the metal being supported on the support of the present invention.

In the catalyst of the present invention, the metal to be supported on the support of the present invention is not particularly limited as long as the metal catalyzes a methanation reaction of carbon monoxide. Examples thereof may include one or more kinds selected from a group consisting of Ni, Ru, Rh, Pd, Pt, Ir, Cu, W, Cs, K, Na, Co, Fe, Ca, Mg, Ba, Sr, and Li.

A method of supporting the metal on the support of the present invention is not particularly limited, and for example, there may be used an impregnation method, an ion exchange method, a co-precipitation method, an electroplating method, or a vapor deposition method. Of those, an impregnation method may be preferably used. In the impregnation method, for example, the metal is supported on the support of the present invention by impregnating the support of the present invention in an aqueous solution containing the metal to be supported, and then removing the solvent of the aqueous solution. In addition, the metal supported on the support of the present invention is preferably reduced before the use of the catalyst of the present invention.

It should be noted that in the catalyst of the present invention, the metal supported on the support of the present invention is mainly supported on the surface of the carbonized material constituting the support of the present invention. On the other hand, the metal to be used for the production of the carbonized material is dispersed in the raw materials. Therefore, in the catalyst of the present invention, the metal derived from the raw materials for the carbonized material, and the metal supported on the carbonized material, exhibit different distributions.

When Ni is supported as the metal that exhibits a catalytic activity for a methanation reaction of carbon monoxide, the catalyst of the present invention may have: a ratio of a peak area in the range of from more than 853.5 eV to 860 eV or less to a peak area in the range of from 850 eV or more to 860 eV or less, the peak areas being obtained by XPS measurement of the electron state of the 2p orbitals of the Ni, (XPS peak area ratio) of 0.5 or more; and a molar ratio of an $H_2$ desorption amount in the range of from 40° C. to 800° C., which is obtained by an $H_2$ temperature-programmed desorption method, to a CO desorption amount in the range of from 40° C. to 800° C., which is obtained by a CO temperature-programmed desorption method, ($H_2$/CO ratio) of 0.3 or more.

In this case, for example, the XPS peak area ratio may be 0.6 or more, or may be 0.7 or more. The upper limit value of the XPS peak area ratio is not particularly limited, and for example, the XPS peak area ratio may be 1.0 or less, or may be less than 1.0.

In addition, for example, the $H_2$/CO ratio may be 0.4 or more, may be 0.5 or more, or may be 0.6 or more. The upper limit value of the $H_2$/CO ratio is not particularly limited, and for example, the $H_2$/CO ratio may be 5 or less.

When the catalyst of the present invention exhibits the XPS peak area ratio and $H_2$/CO ratio described above, the methanation catalytic activity of Ni supported on the support of the present invention is effectively enhanced, and thus the catalyst of the present invention exhibits a particularly excellent methanation catalytic activity.

A methanation reaction apparatus according to one embodiment of the present invention (hereinafter referred to as "apparatus of the present invention") is an apparatus including the metal-supported catalyst described above (that is, the catalyst of the present invention), the apparatus being used for a methanation reaction of carbon monoxide.

The apparatus of the present invention is not particularly limited as long as the apparatus includes the catalyst of the present invention disposed so that the catalyst of the present invention is brought into contact with a gas containing carbon monoxide. That is, for example, the apparatus of the present invention may include: a base material on which the catalyst of the present invention is fixed; and a housing which holds the base material therein so that the catalyst of the present invention is brought into contact with the gas containing carbon monoxide. In this case, for example, ceramics particles or a honeycomb support may be used as the base material. In addition, the apparatus of the present invention may be produced by fixing the catalyst of the present invention to the base material, and causing the resultant to be held in a tubular or rectangular parallelepiped-shaped housing. The mode of the reaction in the apparatus of the present invention is not particularly limited as long as the catalyst of the present invention and the gas to be treated are appropriately brought into contact with each other, and for example, any of a fixed bed system or a fluidized bed system may be employed.

A method according to one embodiment of the present invention (hereinafter referred to as "method of the present invention") is, for example, a method involving performing a methanation reaction of carbon monoxide using the catalyst of the present invention. That is, in this case, the methanation reaction of carbon monoxide is performed by bringing the catalyst of the present invention and the gas containing carbon monoxide into contact with each other, to thereby decrease the concentration of carbon monoxide contained in the gas.

More specifically, the method of the present invention may be, for example, a method involving treating a first gas containing carbon monoxide using the catalyst of the present invention to produce a second gas whose concentration of carbon monoxide is decreased compared to that of the first gas. In this case, a concentration of carbon monoxide in the gas is effectively decreased compared to that before the treatment with the catalyst of the present invention.

The gas to be treated with the catalyst of the present invention is not particularly limited as long as the gas contains carbon monoxide, and for example, the gas may further contain hydrogen. That is, in the method of the present invention, a first gas containing carbon monoxide and hydrogen may be treated using the catalyst of the present invention to produce a hydrogen-containing second gas whose concentration of carbon monoxide is decreased compared to that of the first gas.

More specifically, in a case where a reformed gas is used as the first gas, a hydrogen-containing gas having effectively improved suitability as a fuel for a fuel cell is efficiently produced by bringing the reformed gas and the catalyst of the present invention into contact with each other to effectively decrease the concentration of carbon monoxide in the reformed gas.

In addition, in the method of the present invention, the methanation reaction apparatus including the catalyst of the present invention (that is, the apparatus of the present invention described above) may be used. That is, in this case, a first gas containing carbon monoxide is treated using the apparatus of the present invention to produce a second gas whose concentration of carbon monoxide is decreased compared to that of the first gas.

More specifically, for example, the first gas is made to flow from the upstream end of the apparatus of the present invention into the inside of the apparatus of the present invention, and the first gas and the catalyst of the present invention disposed in the inside of the apparatus of the present invention are brought into contact with each other to perform a methanation reaction of carbon monoxide. Then, the second gas whose concentration of carbon monoxide is decreased compared to that of the first gas is made to flow out from the downstream end of the apparatus of the present invention.

It should be noted that the flow of the gas into the upstream end of the apparatus of the present invention and the flow of the gas out from the downstream end of the apparatus of the present invention may be performed, for example, via pipes connected to the upstream end and the downstream end, respectively. In addition, for example, the downstream end of the apparatus of the present invention may be connected to a fuel cell via the pipe so that the gas produced with the apparatus of the present invention (for example, a hydrogen-containing gas whose concentration of carbon monoxide is decreased compared to that before the treatment) is supplied to the fuel cell through the pipe.

In addition, the apparatus of the present invention to be used in the method of the present invention is not particularly limited as long as the apparatus includes the catalyst of the present invention disposed so that the catalyst of the present invention is brought into contact with the gas containing carbon monoxide as described above. That is, for example, the apparatus of the present invention may include: a base material on which the catalyst of the present invention is fixed; and a housing which holds the base material therein so that the catalyst of the present invention is brought into contact with the gas containing carbon monoxide. In this case, for example, ceramics particles or a honeycomb support may be used as the base material. In addition, the apparatus of the present invention may be produced by fixing the catalyst of the present invention to the base material, and causing the resultant to be held in a tubular or rectangular parallelepiped-shaped housing. The mode of the reaction in the apparatus of the present invention is not particularly limited as long as the catalyst of the present invention and the gas to be treated are appropriately brought into contact with each other, and for example, any of a fixed bed system or a fluidized bed system may be employed.

In addition, the method of the present invention is, for example, a method of selecting, from a plurality of candidate supports, a support for supporting a metal that exhibits a catalytic activity for a methanation reaction of carbon monoxide, the method including: determining, for each of the plurality of candidate supports in a state of supporting Ni, whether or not a ratio of a peak area in the range of from more than 853.5 eV to 860 eV or less to a peak area in the range of from 850 eV or more to 860 eV or less, the peak areas being obtained by XPS measurement of the electron state of the 2p orbitals of the Ni, (XPS peak area ratio) is equal to or higher than a threshold set in advance of 0.5 or more; determining, for each of the plurality of candidate supports in a state of supporting Ni, whether or not a molar ratio of an $H_2$ desorption amount in the range of from 40° C. to 800° C., which is obtained by an $H_2$ temperature-programmed desorption method, to a CO desorption amount in the range of from 40° C. to 800° C., which is obtained by a CO temperature-programmed desorption method, ($H_2$/CO ratio) is equal to or higher than a threshold set in advance of 0.3 or more; and selecting, from the plurality of candidate supports, a support for which it is determined that the ratio of the peak areas is equal to or higher than the threshold, and the molar ratio is equal to or higher than the threshold. That is, in this case, the method of the present invention can be said to be a screening method for a support for supporting a metal that exhibits a catalytic activity for a methanation reaction of carbon monoxide.

The candidate supports are not particularly limited as long as the candidate supports are each capable of supporting a metal that exhibits a catalytic activity for a methanation reaction of carbon monoxide, and for example, supports that are each formed of a carbon material may be preferably used. That is, a plurality of kinds of carbon materials may be used as the plurality of candidate supports.

The carbon material is not particularly limited as long as the material has a carbon structure. Examples thereof may include one or more kinds selected from a group consisting of the carbonized material obtained by carbonizing the raw materials containing the organic substance and the metal described above, carbon black, lignite, activated charcoal, carbon nanotubes, carbon fibers, carbon nanofibers, fullerene, fullerene soot, graphene, and graphite oxide.

That is, as the plurality of candidate supports, there may be used two or more kinds that are different from each other and selected from a group consisting of the carbonized material obtained by carbonizing the raw materials containing the organic substance and the metal, carbon black, lignite, activated charcoal, carbon nanotubes, carbon fibers, carbon nanofibers, fullerene, fullerene soot, graphene, and graphite oxide.

In the method of the present invention, first, each of the plurality of candidate supports is caused to support Ni as a metal that exhibits a catalytic activity for a methanation reaction of carbon monoxide. That is, a plurality of Ni-supported catalysts including different candidate supports supporting Ni are produced.

Next, each of the Ni-supported catalysts is subjected to XPS measurement, and it is determined on the basis of the obtained results whether or not the XPS peak area ratio is equal to or higher than a threshold set in advance of 0.5 or more. The threshold for the XPS peak area ratio is not particularly limited as long as the threshold is 0.5 or more, and for example, the threshold may be 0.6 or more, or may be 0.7 or more. In addition, the upper limit value of the threshold for the XPS peak area ratio is not particularly limited, and for example, the threshold may be 1.0 or less, or may be less than 1.0.

In addition, a CO temperature-programmed desorption method and an $H_2$ temperature-programmed desorption method are each carried out for each of the Ni-supported catalysts, and it is determined on the basis of the obtained results whether or not the $H_2$/CO ratio is equal to or higher than a threshold set in advance of 0.3 or more. The threshold for the $H_2$/CO area ratio is not particularly limited as long as the threshold is 0.3 or more, and for example, the threshold may be 0.4 or more, may be 0.5 or more, or may be 0.6 or more. In addition, the upper limit value of the threshold for the $H_2$/CO area ratio is not particularly limited, and for example, the threshold may be 5 or less.

In the method of the present invention, from the plurality of candidate supports, a candidate support having such characteristics that the XPS peak area ratio is equal to or higher than the threshold, and the $H_2$/CO ratio is equal to or higher than the threshold, is selected as a preferred support for supporting a metal that exhibits a catalytic activity for a methanation reaction of carbon monoxide. Therefore, according to the method of the present invention, a support that effectively enhances the methanation catalytic activity of a metal supported thereon is efficiently selected from the plurality of candidate supports.

Next, specific examples according to those embodiments are described.

Example 1

[Production of Support for Supporting Metal]

First, raw materials to be carbonized were prepared. That is, a phenol resin (for spinning, manufactured by Gunei Chemical Industry Co., Ltd.) and cobalt phthalocyanine (purity: 90%, manufactured by Tokyo Chemical Industry Co., Ltd.) were mixed in acetone so that the weight ratio of cobalt (Co) to the phenol resin was 3 wt %. The resultant mixture was subjected to ultrasonic stirring for 30 minutes, and the solvent was removed using an evaporator. After that, the mixture was dried under reduced pressure at 70° C. overnight to yield the raw materials.

Next, the raw materials prepared as described above were carbonized. That is, 1 g of the raw materials was placed in a quartz boat, and the quartz boat was placed in the center of a quartz reaction tube ($\phi$23.5 mm×600 mm). Then, the quartz reaction tube was purged with a high-purity nitrogen gas at a flow rate of 500 mL/min for 20 minutes.

After that, the quartz reaction tube was heated using an infrared image furnace (RHL410P, manufactured by Shinku Riko K.K.) under a stream of a high-purity nitrogen gas (500 mL/min), and its temperature was increased at a rate of temperature increase of 10° C./min to 1,000° C. Further, the quartz reaction tube was kept at 1,000° C. for 1 hour to carbonize the raw materials.

The carbonized material thus obtained by the carbonization of the raw materials was pulverized in a mortar. Further, 500 mg of the pulverized carbonized material and 10 pulverizing balls were put into a vessel, and pulverization treatment was performed using a planetary ball mill at a rotation speed of 750 rpm for 90 minutes. After that, the pulverized carbonized material was sieved with a sieve having an opening of 106 μm, and the carbonized material that had passed through the sieve was collected.

Next, the carbonized material, concentrated hydrochloric acid, and a stirring bar were put into a vial, followed by stirring using a magnetic stirrer for 2 hours, and then followed by suction filtration. This operation was repeated three times, and then the carbonized material was dried under reduced pressure at 80° C. overnight. Then, the carbonized material after the drying was obtained as a support for supporting a metal (NSC: nanoshell carbon).

[Production of Metal-Supported Catalyst]

Nickel (Ni) was supported on NSC produced as described above by an impregnation method involving using an aqueous solution of nickel nitrate ($Ni(NO_3)_2 \cdot 6H_2O$) (Special Grade reagent, manufactured by Wako Pure Chemical Industries, Ltd.).

That is, the aqueous solution of nickel nitrate was weighed so that the weight ratio of Ni to NSC became 10 wt %. Next, the aqueous solution of nickel nitrate, NSC, and 200 mL of distilled water were charged into a recovery flask having a volume of 500 mL, followed by ultrasonic stirring for 10 minutes.

Further, the distilled water was evaporated from the mixture with a rotary evaporator (hot water bath temperature: 60° C., rotation speed: 8 rpm), and the residue was dried under reduced pressure at 80° C. overnight. After that, the temperature was increased at a rate of temperature increase of 20° C./min to 350° C. with a vertical image furnace (RHL-E25N, manufactured by Shinku Riko K.K.) under a stream of a 10% $H_2$ gas (Ar:$H_2$=450:50 (mL/min)), and kept at 350° C. for 1 hour, to thereby perform reduction. Thus, a metal-supported catalyst formed of NSC and Ni supported on the NSC (Ni/NSC) was obtained.

In addition, as a comparative example, carbon black (Vulcan XC-72R, manufactured by CABOT CORPORATION) (XC) was used in place of NSC as the support for supporting a metal, and a metal-supported catalyst in which Ni was supported on the XC (Ni/XC) was produced in the same manner as described above.

In addition, as another comparative example, lignite (LY) was used in place of NSC as the support for supporting a metal, and a metal-supported catalyst in which Ni was supported on the LY (Ni/LY) was produced by an ion exchange method involving utilizing a surface functional group present in the LY in a large amount.

It should be noted that the amount of Ni to be supported in Ni/XC and Ni/LY was adjusted so that the particle size of Ni supported in the Ni/XC and the particle size of Ni supported in the Ni/LY were about the same as the particle size of Ni supported in Ni/NSC. As a result, the weight ratio of Ni to XC in Ni/XC was determined to be 8 wt %, and the weight ratio of Ni to LY in Ni/LY was determined to be 20 wt %.

[Transmission Electron Microscopic Observation]

In order to observe the state of supported Ni and measure the Ni particle size, the metal-supported catalysts were each observed using a transmission electron microscope (JEM-2010, manufactured by JEOL Ltd.) (TEM). That is, 1 mg of each metal-supported catalyst was put into a vial together with 5 mL of methanol, and subjected to ultrasonic stirring for 10 minutes to disperse the metal-supported catalyst in methanol. After that, 2 μL of the solution containing the metal-supported catalyst were placed on a microgrid made of copper, and the grid was put into the TEM, followed by observation at an accelerating voltage of 200 kV.

On the basis of the obtained TEM image, the particle size of Ni supported on the metal-supported catalyst was measured. That is, the diameters of 300 Ni particles in a TEM image at a magnification of 200K were measured, and their average value was calculated as the Ni particle size. In addition, a support for supporting a metal having no metal supported thereon (NSC) was similarly subjected to TEM observation.

[X-Ray Diffraction]

In order to observe the state of supported Ni and measure the Ni crystallite size, the metal-supported catalysts were each subjected to X-ray diffraction (XRD). That is, each metal-supported catalyst was uniformly dispersed and placed on a holder made of glass, and subjected to XRD measurement using an XRD apparatus (XRD-6100, manufactured by SHIMADZU CORPORATION) under the conditions of CuKα, 32 kV, 20 mA, scanning range: 5 to 90°, and scanning step: 0.01°. The Ni crystallite size was calculated using an Ni (220) peak around 52.0°.

Figure 4A:
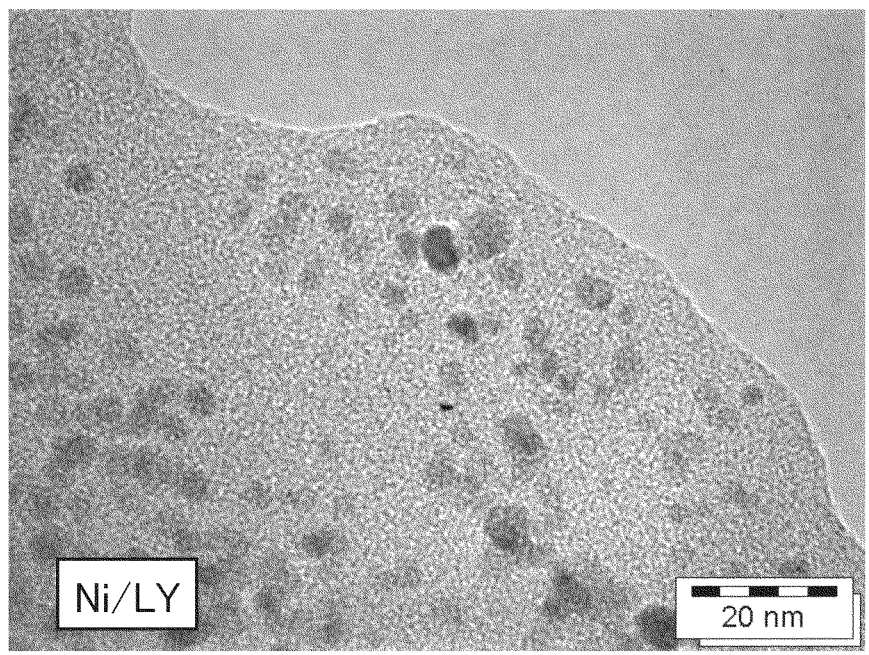
FIG. 4A is an explanatory diagram showing an example of the result of observation of another metal-supported catalyst used for comparison, with a transmission electron microscope.
Figure 4B:
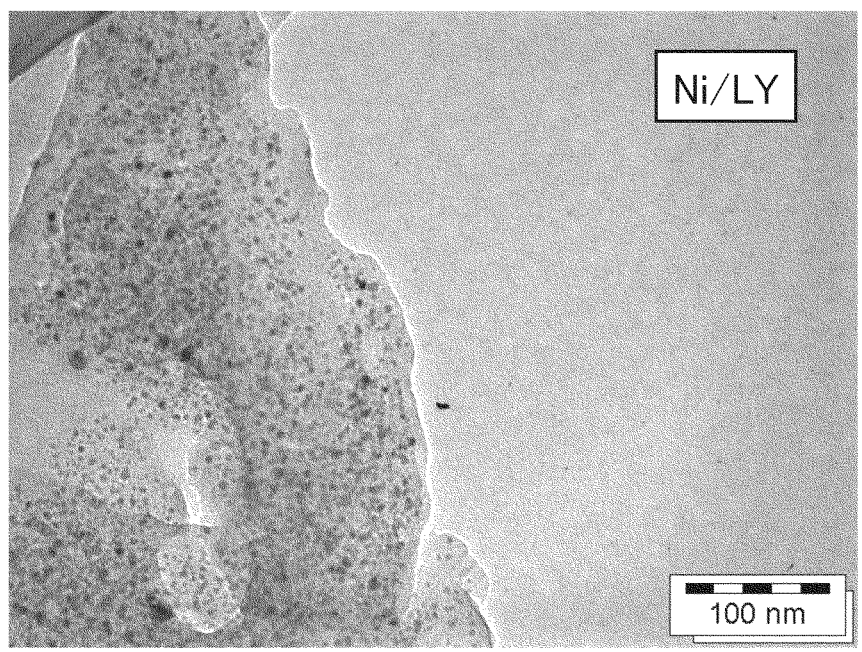
FIG. 4B is an explanatory diagram showing another example of the result of observation of another metal-supported catalyst used for comparison, with a transmission electron microscope.

FIG. 1A to FIG. 4B show the results of the TEM observation. FIG. 1A and FIG. 1B are TEM images of NSC, FIG. 2A and FIG. 2B are TEM images of Ni/NSC, FIG. 3A and FIG. 3B are TEM images of Ni/XC, and FIG. 4A and FIG. 4B are TEM images of Ni/LY.

Figure 1B:
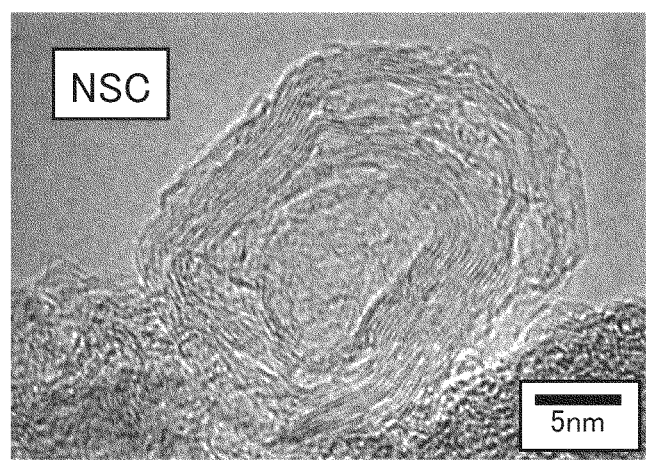
FIG. 1B is an explanatory diagram showing another example of the result of observation of the support for supporting a metal according to the one embodiment of the present invention with a transmission electron microscope.
Figure 2A:
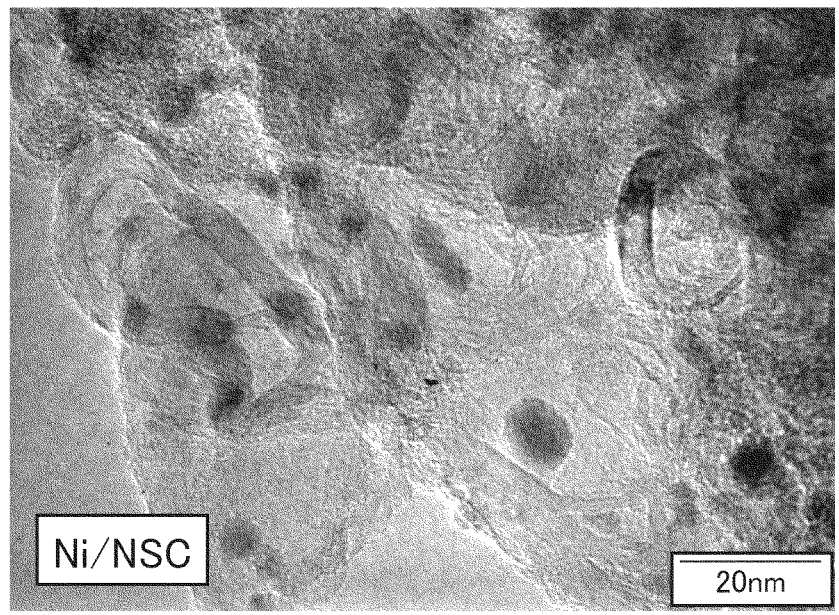
FIG. 2A is an explanatory diagram showing an example of the result of observation of a metal-supported catalyst according to one embodiment of the present invention with a transmission electron microscope.
Figure 2B:
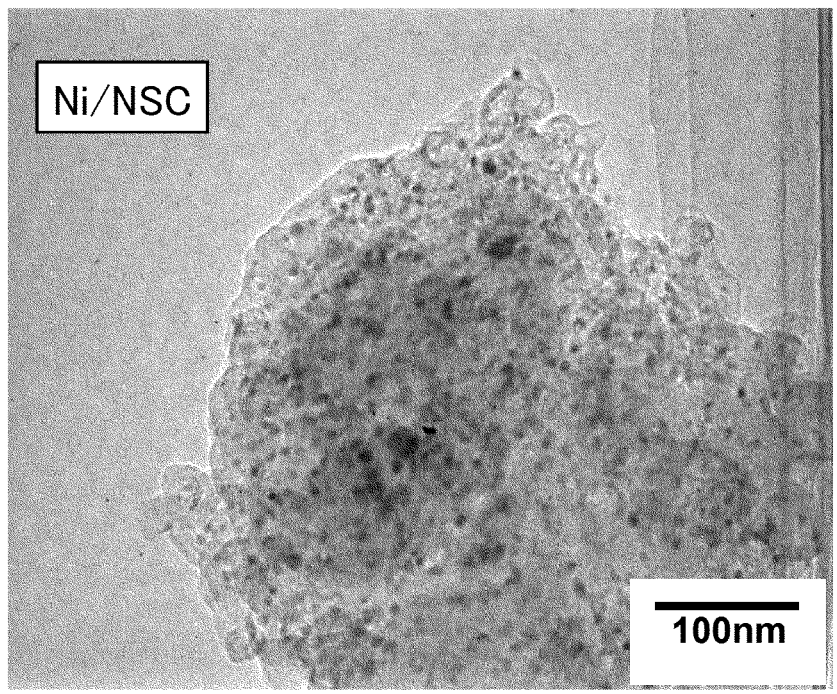
FIG. 2B is an explanatory diagram showing another example of the result of observation of the metal-supported catalyst according to the one embodiment of the present invention with a transmission electron microscope.
Figure 3A:
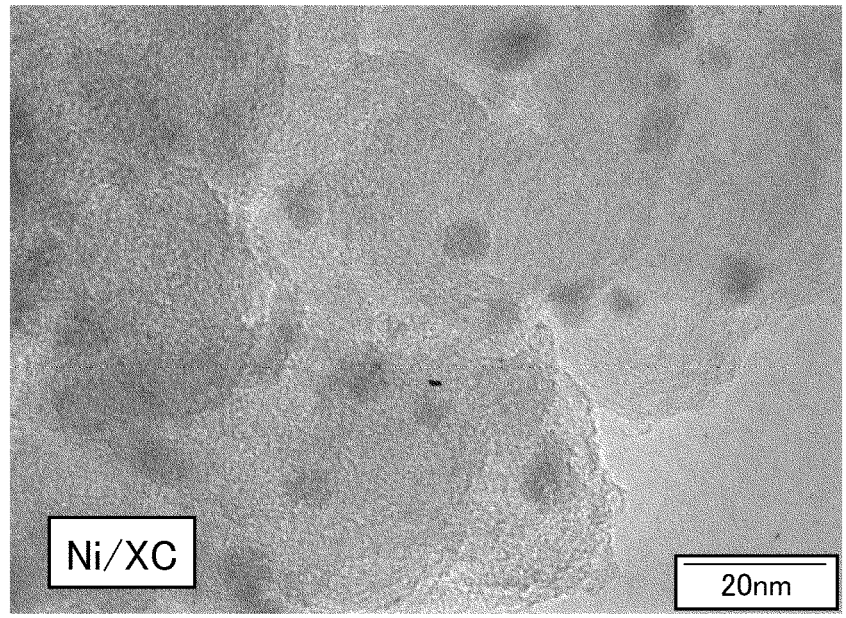
FIG. 3A is an explanatory diagram showing an example of the result of observation of a metal-supported catalyst used for comparison, with a transmission electron microscope.
Figure 3B:
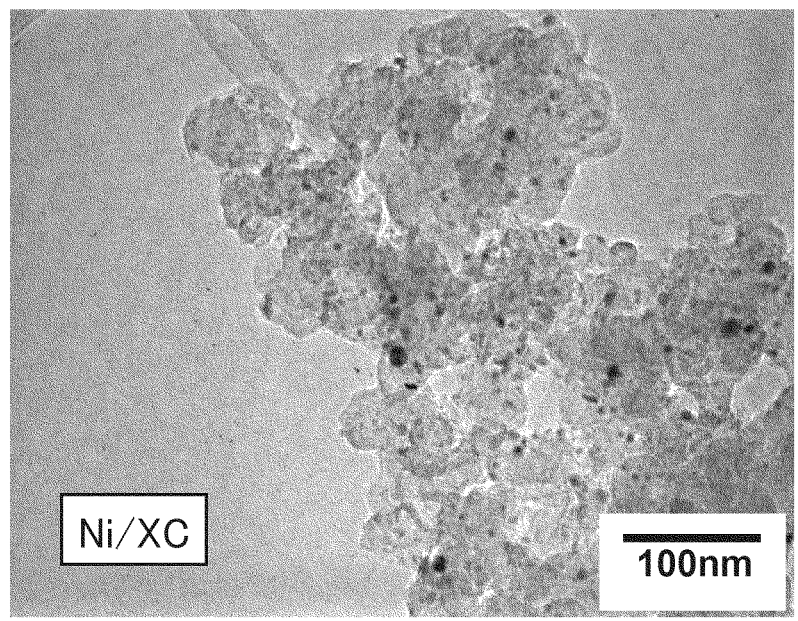
FIG. 3B is an explanatory diagram showing another example of the result of observation of the metal-supported catalyst used for comparison, with a transmission electron microscope.

As shown in FIG. 1A and FIG. 1B, NSC had a carbon structure (graphite-like structure) including a nanoshell structure specifically formed by carbonizing raw materials containing an organic substance and a metal. Specifically, as shown in FIG. 1A and FIG. 1B, the nanoshell structure was a graphite structure-like turbostratic structure that had been developed in the form of an onion-like laminate around Co fine particles contained in the raw materials. In addition, as shown in FIG. 2A and FIG. 2B, in Ni/NSC, Ni fine particles were supported on NSC, which had a carbon structure as described above, in a state of being dispersed.

In addition, as shown in FIG. 3A, FIG. 3B, FIG. 4A, and FIG. 4B, in Ni/XC and Ni/LY, Ni fine particles were supported on XC and LY, which had clearly different carbon structures from that of NSC, in a state of being dispersed as in Ni/NSC.

Figures 5, 6:
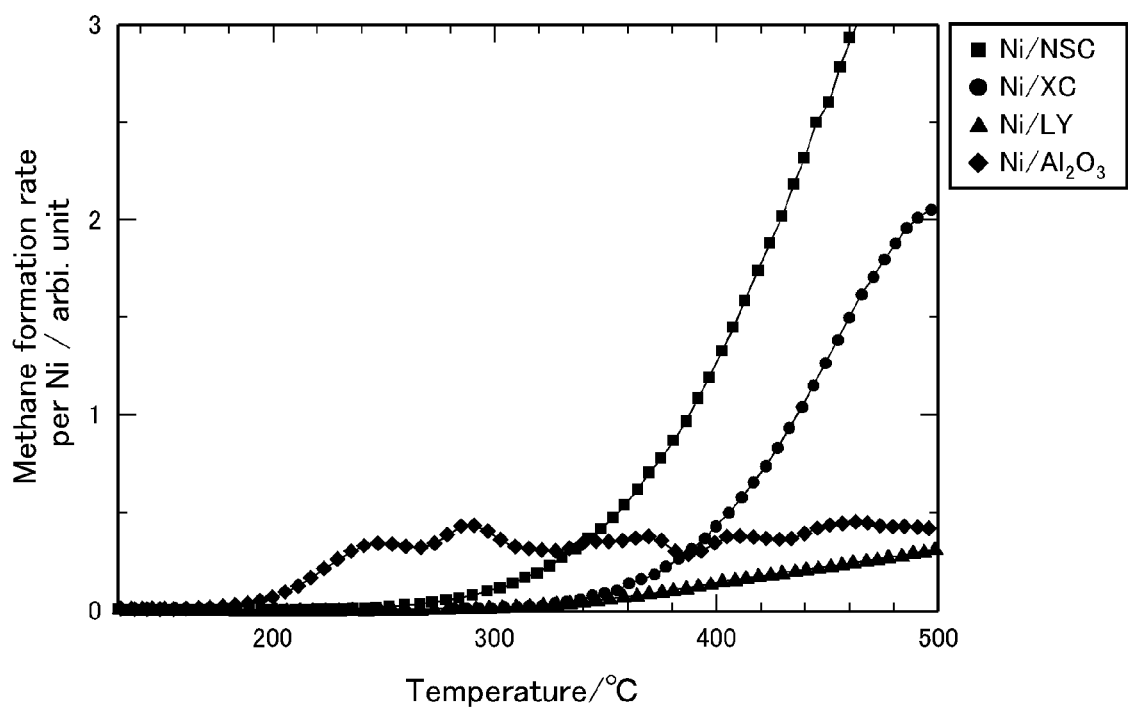
FIG. 5 is an explanatory diagram showing examples of the results of evaluation of the particle size and crystallite size of a metal supported on metal-supported catalysts in an Example according to one embodiment of the present invention.
FIG. 6 is an explanatory diagram showing examples of the results of evaluation of the methanation catalytic activities of metal-supported catalysts in an Example according to one embodiment of the present invention.

FIG. 5 shows the results of evaluation of the Ni particle sizes and Ni crystallite sizes of the metal-supported catalysts. As shown in FIG. 5, the three kinds of metal-supported catalysts had about the same Ni particle size and Ni crystallite size. That is, it was conceivable that, when a difference was found in characteristic among those three kinds of metal-supported catalysts, the difference was not due to differences in Ni particle size and Ni crystallite size, but due to another factor.

Example 2

[Methanation Catalytic Activity]

A methanation reaction of carbon monoxide using metal-supported catalyst was performed with a temperature-programmed desorption spectrometer (Multitask TPD, manufactured by BEL Japan, Inc.) to evaluate the methanation catalytic activity of the metal-supported catalyst.

As the metal-supported catalyst, each of the following four kinds were used: Ni/NSC, Ni/XC, Ni/LY, and a metal-supported catalyst (Ni/$Al_2O_3$) obtained by supporting Ni on alumina ($Al_2O_3$). The Ni/$Al_2O_3$ was produced using alumina in place of NSC as the support for supporting a metal by supporting Ni on alumina in the same manner as in the case of Ni/NSC. The weight ratio of Ni to alumina in Ni/Al$_2$O$_3$ was 10 wt %.

First, 20 mg of the metal-supported catalyst were loaded into a reaction tube, and the inside of the system was evacuated using a turbomolecular pump (manufactured by Mitsubishi Heavy Industries, Ltd.). Next, under a stream of an H$_2$ gas (50 mL/min), the reaction tube was heated to increase its temperature at a rate of temperature increase of 10° C./min to 350° C., and the reaction tube was kept at 350° C. for 30 minutes, to thereby perform prereduction. After that, the inside of the system was purged with an He gas (50 mL/min) for 10 minutes, to thereby discharge the H$_2$ gas remaining in the system and to decrease the temperature of the reaction tube to 40° C.

Further, while a mixed gas containing carbon monoxide ((H$_2$+CO)/He) (H$_2$: 24 mL/min, CO: 8 mL/min, He: 18 mL/min) was made to flow through the system, the temperature of the reaction tube was increased at a rate of temperature increase of 10° C./min to 800° C., and the amount of methane (CH$_4$) formed during the increase was measured with a quadrupole mass spectrometer (manufactured by CANON ANELVA CORPORATION).

FIG. 6 shows the results of evaluation of the methanation catalytic activities of the metal-supported catalysts. In FIG. 6, the horizontal axis represents temperature (° C.), the vertical axis represents methane formation reaction rate per unit weight (1 g) of Ni supported on a metal-supported catalyst, and the square, the circle, the triangle, and the rhombus represent the results of Ni/NSC, Ni/XC, Ni/LY, and Ni/Al$_2$O$_3$, respectively.

As shown in FIG. 6, in the cases of using Ni/XC and Ni/LY, methane was formed at about 280° C. or more. On the other hand, in the case of using Ni/NSC, methane was formed at about 240° C. or more.

That is, the temperature at which the methanation reaction started was lower in the case of using Ni/NSC than in the cases of using Ni/XC and Ni/LY. In other words, it was demonstrated that Ni/NSC was capable of allowing the methanation reaction to start at a lower temperature than Ni/XC and Ni/LY.

On the other hand, the methanation reaction started at a lower temperature (about 220° C.) in the case of using Ni/Al$_2$O$_3$ than in the case of using Ni/NSC. However, at temperatures of 340° C. or more, the methane formation rate in the case of using Ni/Al$_2$O$_3$ was markedly lower than that in the case of using Ni/NSC.

Thus, it was confirmed that the use of Ni/NSC as the catalyst for methanation of carbon monoxide enabled effective removal of carbon monoxide contained in a hydrogen-containing gas and efficient production of a hydrogen-containing gas whose concentration of carbon monoxide was effectively decreased.

Example 3

[X-Ray Photoelectron Spectroscopy]

In order to grasp the electron state of Ni supported on a metal-supported catalyst, X-ray photoelectron spectroscopy (XPS) was performed for each of Ni/NSC, Ni/XC, and Ni/LY. That is, an XPS apparatus (AXIS NOVA, manufactured by SHIMADZU CORPORATION) was used, the metal-supported catalyst was placed on a carbon tape attached to an aluminum piece, and the whole was introduced into the apparatus. Then, XPS measurement was performed using AlKα as an X-ray source under the conditions of 15 kV and 10 mA.

Figure 7A:
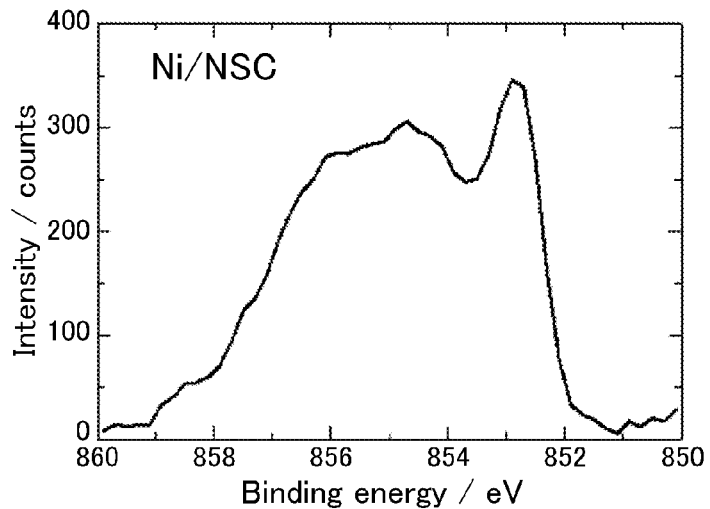
FIG. 7A is an explanatory diagram showing an example of the result of evaluation of a metal-supported catalyst according to one embodiment of the present invention by X-ray photoelectron spectroscopy.
Figure 7B:
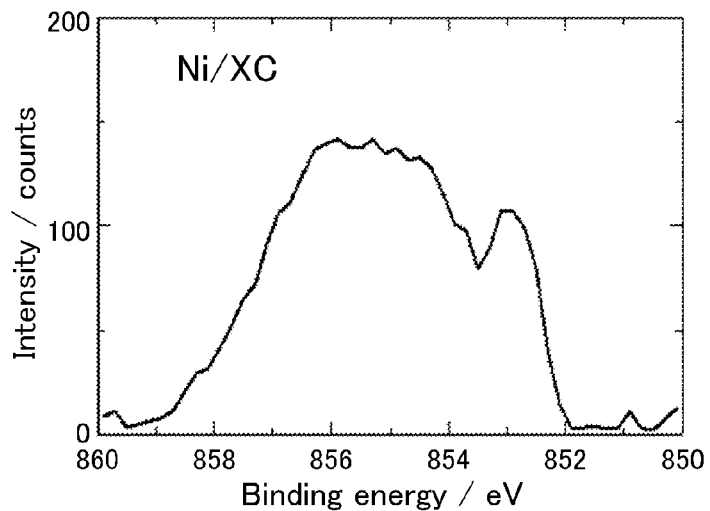
FIG. 7B is an explanatory diagram showing an example of the result of evaluation of a metal-supported catalyst used for comparison by X-ray photoelectron spectroscopy.
Figure 7C:
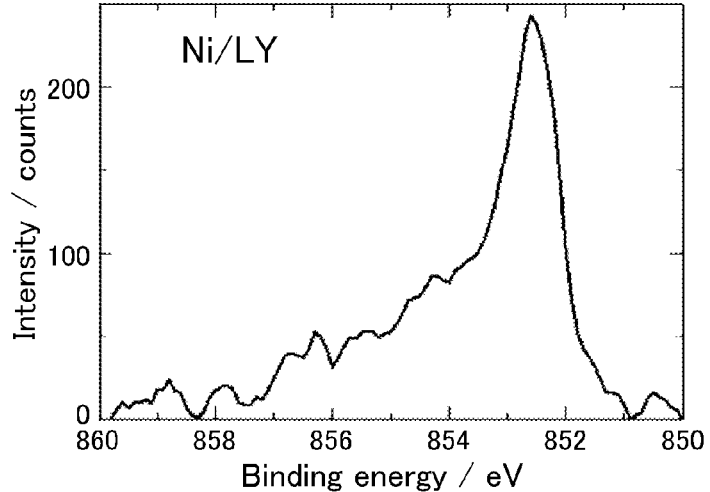
FIG. 7C is an explanatory diagram showing an example of the result of evaluation of another metal-supported catalyst used for comparison by X-ray photoelectron spectroscopy.

FIG. 7A, FIG. 7B, and FIG. 7C show the results of the XPS measurement of Ni/NSC, Ni/XC, and Ni/LY, respectively. As shown in FIG. 7A to FIG. 7C, it was confirmed that the shape of the 2p spectrum of Ni changed, that is, the electron state of the Ni changed, depending on the kind of support on which Ni was supported.

Specifically, for example, Ni/NSC and Ni/XC each showed a peak at 852.8 eV corresponding to metal Ni, and also showed peaks in a higher binding energy region. On the other hand, Ni/LY showed a main peak at 852.8 eV corresponding to metal Ni, and showed only small peaks in the higher binding energy region.

In view of the foregoing, in order to quantitatively confirm such a difference, the three kinds of metal-supported catalysts were compared to each other in terms of ratio of a peak area in the higher binding energy region to a peak area around 852.8 eV corresponding to metal Ni.

Specifically, the binding energy at which peaks underwent transition from the lower binding energy state (metal Ni) to the higher binding energy state was defined to be 853.5 eV, and the ratio of a peak area in the range of from more than 853.5 eV to 860 eV or less to a peak area in the range of from 850 eV or more to 860 eV or less (XPS peak area ratio described above) was determined.

The results were as follows: the XPS peak area ratio of Ni/LY was 0.44, whereas the XPS peak area ratio of Ni/NSC was 0.73 and the XPS peak area ratio of Ni/XC was 0.81. Therefore, the XPS peak area ratio of 0.5 or more was considered as one of the reasons that Ni/NSC exhibited an excellent methanation catalytic activity.

Example 4

[Temperature-Programmed Desorption Method]

CO and H$_2$ temperature-programmed desorption methods (TPD) were carried out for each of Ni/NSC and Ni/XC using a temperature-programmed desorption spectrometer (Multi-task TPD, manufactured by BEL Japan, Inc.). It should be noted that an exact spectrum of Ni/LY was difficult to obtain because LY had a thermal decomposition temperature of about 600° C.

20 mg of the metal-supported catalyst were loaded into a reaction tube, and the inside of the system was evacuated using a turbomolecular pump (manufactured by Mitsubishi Heavy Industries, Ltd.). Next, under a stream of an H$_2$ gas (50 mL/min), the reaction tube was heated to increase its temperature at a rate of temperature increase of 10° C./min from 40° C. to 350° C., and the reaction tube was kept at 350° C. for 30 minutes, to thereby perform prereduction. After that, the inside of the system was purged with an He gas (50 mL/min) for 10 minutes, to thereby discharge the H$_2$ gas remaining in the system and to decrease the temperature of the reaction tube to 40° C.

Further, in this system, under a stream of a 20% H$_2$ gas (H$_2$:He=10:40 (mL/min)) or a 16% CO gas (CO:He=8:42 (mL/min)), the reaction tube was kept at 40° C. for 30 minutes, to thereby adsorb H$_2$ or CO onto the metal-supported catalyst. After that, the inside of the system was purged with a He gas (50 mL/min) for 10 minutes, to thereby discharge the H$_2$ gas or CO gas remaining in the system.

Further, the reaction tube was heated, and H$_2$ or CO that was desorbed during the period when the temperature of the reaction tube increased at a rate of temperature increase of 10° C./min from 40° C. to 800° C. was confirmed with a quadrupole mass spectrometer (manufactured by CANON ANELVA CORPORATION).

[H₂ and CO Desorption Amounts]

On the basis of the results obtained as described above, the desorption amount of $H_2$ and desorption amount of CO from each metal-supported catalyst were each determined. That is, a calibration curve showing a correlation between the peak area of $H_2$ or CO and the $H_2$ or CO desorption amount was created by an $H_2$ temperature-programmed desorption method or CO temperature-programmed desorption method using a standard substance ($MgH_2$ or $CaC_2O_4 \cdot H_2O$) for which the $H_2$ or CO desorption amount was able to be theoretically determined.

Specifically, with regard to $H_2$, the $H_2$ temperature-programmed desorption method was carried out using a plurality of standard samples containing $MgH_2$ at different ratios (samples prepared by mixing $MgH_2$ and alumina ($Al_2O_3$) at different ratios, more specifically, samples from each of which 500 μmol or 1,000 μmol of $H_2$ were to be theoretically desorbed per 1 g of the sample), and a correlation between the peak area of $H_2$ obtained by thermally decomposing the $MgH_2$ and the theoretical $H_2$ desorption amounts from the standard samples was determined.

In addition, with regard to CO, the CO temperature-programmed desorption method was carried out using a plurality of standard samples containing $CaC_2O_4 \cdot H_2O$ at different ratios (samples prepared by mixing $CaC_2O_4 \cdot H_2O$ and alumina ($Al_2O_3$) at different ratios, more specifically, samples from each of which 500 μmol or 750 μmol of CO were to be theoretically desorbed per 1 g of the sample), and a correlation between the peak area of CO obtained by thermally decomposing the $CaC_2O_4 \cdot H_2O$ and the theoretical CO desorption amounts from the standard samples was determined.

Then, on the basis of the thus obtained calibration curves, and the peak area of $H_2$ and peak area of CO of each metal-supported catalyst described above obtained by the $H_2$ temperature-programmed desorption method and the CO temperature-programmed desorption method, the $H_2$ desorption amount and CO desorption amount from the metal-supported catalyst were respectively determined.

It should be noted that the supports of the metal-supported catalysts were carbon materials, and hence the CO desorption amount of each of the metal-supported catalysts was determined as a value obtained by subtracting the CO desorption amount measured for the support (NSC and XC) by the CO temperature-programmed desorption method from the CO desorption amount measured for the metal-supported catalyst (Ni/NSC and Ni/XC) by the CO temperature-programmed desorption method.

Further, the molar ratio of the $H_2$ desorption amount in the range of from 40 to 800° C., which was obtained by the $H_2$ temperature-programmed desorption method, to the CO desorption amount in the range of from 40 to 800° C., which was obtained by the CO temperature-programmed desorption method, (the $H_2$/CO ratio described above) was calculated.

FIG. 8A and FIG. 8B show the results of the $H_2$ temperature-programmed desorption method and the CO temperature-programmed desorption method, respectively. In FIG. 8A and FIG. 8B, the horizontal axis represents temperature (° C.), the vertical axis represents $H_2$ or CO desorption amount per unit weight (1 g) of Ni supported on the metal-supported catalyst (nA/g-Ni), the solid line represents the result of Ni/NSC, and the broken line represents the result of Ni/XC.

FIG. 9 shows the $H_2$ desorption amount and CO desorption amount (mmol/g-Ni) per unit weight (1 g) of Ni supported on each of the metal-supported catalysts, calculated from results of the $H_2$ temperature-programmed desorption method and the CO temperature-programmed desorption method, and $H_2$/CO ratio calculated from the desorption amounts.

As shown in FIG. 8A and FIG. 8B, each of the $H_2$ desorption amount and CO desorption amount of Ni/NSC was markedly large compared to that of Ni/XC. That is, each of the $H_2$ adsorption amount and CO adsorption amount of Ni/NSC was confirmed to be markedly large compared to that of Ni/XC. In particular, the $H_2$ desorption amount of Ni/NSC was about 5.4 times as large as that of Ni/XC. That is, Ni/NSC was confirmed to be particularly excellent in $H_2$ adsorption.

In addition, as shown in FIG. 9, the $H_2$/CO ratio of Ni/XC was 0.21, whereas that of Ni/NSC was 0.68. That is, the $H_2$/CO ratio of Ni/NSC was markedly high compared to that of Ni/XC.

In this context, in the methanation reaction in which CO is hydrogenated to form $CH_4$, it is considered that the amount of $H_2$ held on the surface of the metal-supported catalyst is preferably large. That is, it is important in the hydrogenation of CO to suppress the deposition of carbon on the surface of the catalyst (Bourdourd reaction).

Accordingly, for example, it is desired that $CH_4$ be formed through an attack by hydrogen before CO adsorbed on the surface of the catalyst forms surface carbide structures and the surface carbide structures are further bound to each other two-dimensionally to form deposited carbon. In addition, it is considered that hydrogen accumulated in the metal-supported catalyst can be effectively utilized as the hydrogen.

In this regard, Ni/NSC had a large amount of hydrogen adsorbed on its surface as described above. Besides, a large amount of hydrogen remained in Ni/NSC even at 400° C. or more. That is, it was considered that the presence of hydrogen accumulated in Ni/NSC effectively enhanced the methanation catalytic activity of the Ni/NSC. Therefore, the $H_2$/CO ratio of 0.3 or more, which reflected its excellent ability to accumulate hydrogen, was considered as one of the reasons that Ni/NSC exhibited an excellent methanation catalytic activity.

The invention claimed is:
1. A metal-supported catalyst, comprising:
a support formed of a carbonized material obtained by carbonizing raw materials containing an organic substance and a first metal; and
a second metal that exhibits a catalytic activity for a methanation reaction of carbon monoxide, the second metal being supported on the support,
wherein the first metal is dispersed in the carbonized material and the second metal is mainly supported on the surface of the carbonized material, and
wherein the first metal is one or more kinds selected from the group consisting of Sc, Ti, V, Cr, Co, Ni, Cu, Zn, Y, Ru, Rh, Pd, lanthanides, and actinides.
2. The metal-supported catalyst according to claim 1, wherein the metal that exhibits a catalytic activity for a methanation reaction of carbon monoxide comprises one or more kinds selected from the group consisting of Ni, Ru, Rh, Pd, Pt, Ir, Cu, W, Cs, K, Na, Co, Fe, Ca, Mg, Ba, Sr, and Li.
3. The metal-supported catalyst according to claim 2, wherein the metal that exhibits a catalytic activity for a methanation reaction of carbon monoxide comprises Ni.
4. The metal-supported catalyst according to claim 3, wherein the support has:
a ratio of a peak area in a range of from more than 853.5 eV to 860 eV or less to a peak area in a range of from 850 eV or more to 860 eV or less of 0.5 or more, the peak areas being obtained by XPS measurement of an electron state of 2p orbitals of the Ni; and a molar ratio of an $H_2$ desorption amount in a range of from 40° C. to 800° C., which is obtained by an $H_2$ temperature-programmed desorption method, to a CO desorption amount in a range of from 40° C. to 800° C., which is obtained by a CO temperature-programmed desorption method, of 0.3 or more.

5. The metal-supported catalyst according to claim 4, wherein said ratio of a peak area is 0.6 or more.

6. The metal-supported catalyst according to claim 4, wherein said ratio of a peak area is 0.7 or more.

7. The metal-supported catalyst according to claim 4, wherein said molar ratio is 0.4 or more.

8. The metal-supported catalyst according to claim 4, wherein said molar ratio is 0.5 or more.

9. The metal-supported catalyst according to claim 1, wherein the first metal is different from the second metal.

10. A methanation reaction apparatus, comprising the metal-supported catalyst according to claim 1, wherein the methanation reaction apparatus is used for a methanation reaction of carbon monoxide.

11. A method, comprising performing a methanation reaction of carbon monoxide using the metal-supported catalyst according to claim 1.

12. The method according to claim 11, comprising treating a first gas containing carbon monoxide to produce a second gas whose concentration of carbon monoxide is decreased compared to that of the first gas.

13. The method according to claim 12, wherein the first gas and the second gas each further contain hydrogen.

14. The method according to claim 11, wherein the method uses a methanation reaction apparatus including the metal-supported catalyst.

* * * * *